United States Patent
Sinha et al.

[11] Patent Number: 6,150,367
[45] Date of Patent: Nov. 21, 2000

[54] 1-[4-ARYLPIPERAZIN-1-YL]-3-[2-OXOPYRROLIDIN/PIPERIDIN-1-YL] PROPANES AND THEIR USE IN MEDICAL TREATMENTS

[75] Inventors: Neelima Sinha; Sanjay Jain; Anil Kumar Saxena; Nitya Anand; Ram Mohan Saxena; Mangal Prasad Dubey; Madhur Ray, all of Lucknow; Gyanendra K. Patnaik, deceased, late of Lucknow, all of India, by Pushpa Patnaik, Hermut Kumar Patnaik, Sumeet Patnaik, executors

[73] Assignee: Council of Scientific & Industrial Research, New Delhi, India

[21] Appl. No.: 08/954,516

[22] Filed: Oct. 20, 1997

[51] Int. Cl.⁷ .................. A61K 31/496; C07D 401/06; C07D 401/14; C07D 403/06
[52] U.S. Cl. .................. 514/253.12; 514/253.09; 514/254.01; 544/360; 544/364; 544/372
[58] Field of Search ................. 544/360, 364, 544/372; 514/252, 253.09, 253.12, 254.01

[56] References Cited

U.S. PATENT DOCUMENTS

| | | | |
|---|---|---|---|
| 4,668,687 | 5/1987 | Yevich et al. | 514/252 |
| 5,180,726 | 1/1993 | Carlier et al. | 514/252 |
| 5,599,815 | 2/1997 | Fukuda et al. | 514/254 |

OTHER PUBLICATIONS

Medline Abstract for Cooke et al, *Vascular Medicine* 2 (1), pp. 1–7 (1997), 1998.
Rachman et al, *Diabetic Medicine*, 12 (6) pp. 467–478, 1995.
Drug Evaluations by the American Medical Association, pp. 575–579, 1993.

*Primary Examiner*—Emily Bernhardt
*Attorney, Agent, or Firm*—Pennie & Edmonds LLP

[57] ABSTRACT

A chemical compound and composition of Formula 1:

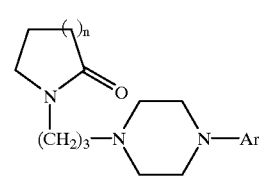

wherein Ar represents a phenyl ring substituted by the groups like halo, alkoxy, alkyl or heteroaryl, n=1 or n=2; said compounds and compositions as being useful therapeutic agents for hypertension, ischemic, cardiovascular and other adrenergic receptor related disorders.

12 Claims, 4 Drawing Sheets

X = O, S

1-[4-ARYLPIPERAZIN-1-YL]-3-[2-OXOPYRROLIDIN/PIPERIDIN-1-YL] PROPANES AND THEIR USE IN MEDICAL TREATMENTS

FIELD OF THE INVENTION

The present invention relates to a process for the synthesis of novel 1-[4-Arylpiperazin-1yl]-3-[2-oxopyrrolidin-1yl] propanes and 1-[4-Arylpiperazin-1yl]-3-[2-oxopyrrolidin-1yl]propanes which can be used as therapeutic agents for hypertension, ischemia, cardiovascular and other adrenergic receptors related disorders. More, particularly the present invention relates, to a process for the synthesis of 1-[4-Arylpiperarzin-1-yl]-3-[2-oxopyrrolidin-1-yl]propanes and 1-[4-Arylpiperazin-1-yl]-3-[2-oxopiperidin-1-yl]propanes, and to their use in medicine. This invention provides the compounds of the formula 1:

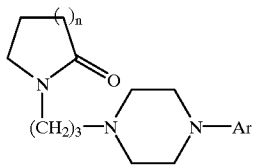

wherein Ar represents a phenyl ring substituted by the groups like halo, alkoxy, alkyl or heteroaryl and n=1 or n=2.

The compounds of the invention have shown to possess antihypertensive activity in different test models. The compounds also prevent post-ischemic reperfusion injury and may be useful in the treatment of hypertension, diseases arising out of alterations/impairment in central/peripheral circulations and adrenergic receptors systems, such as myocardial ischemia, myocardial infarction (MI), agina pectoris, any cardiac surgical interventions renal ischemia, circulatory insufficiency in extremities, stroke and trauma.

A general method of preparation of the inventive compounds starts from the condensation of 1-bromo-3-chloropropane with 2-pyrrolidone or 2-poperiodone to give the key intermediate 1-chloro-3-[2-oxopyrrolindin-1-yl] propanes (n=1) of formula 3 or 1-chloro-3-[2-oxopiperidin-1-yl]propanes (n=2) followed by its condensation with different 1-substituted piperazines of formula 4 to get the compounds of formula 1 and the said method is the subject matter of the co-pending U.S. application Ser. No. 08/960, 335. According to the method, the process of which starts from the condensation of 1-bromo-3-chloropropane with different 1-substituted piperazines of formula 4 to give the 1-chloro-3-(4-substituted piperazin-1-yl)propanes of formula 5 followed by their condensation with 2-pyrrolidone or 2-piperidone of formula 2 to get the compounds of formula 1 (formulae 2 to 5 arte shown in scheme 1 of the accompany drawings).

The compounds of the present invention can be used as pharmaceutical compositions comprising compounds of the present invention with a suitable pharmaceutical carrier. Preferably, these compositions are used to produce antihypertensive and antiischemic activities and contain an effective amount of hte compounds useful in the method of the invention. The most preferred compound of the invention is 1-[4-(4-flourophenyl)piperazin-1yl]-3-[2-oxopyrrolidin-1-yl]propane.

BACKGROUND OF THE INVENTION

Hypertension is the most common of all cardiovascular diseases afflicting about 10–20% adult population. Several classes of drugs may be used in the treatment and management of hypertension such as alpha-adrenoceptor antagonists. ACE inhibitors, angiotensin I chymase inhibitors, renin inhibitors, angiotensin II antagonists, vasopressin $V_1$ antagonists, endothelin antagonists, endothelin-converting enzyme inhibitors, potassium channel activators, calcium channels antagonists, adenosine A[2] agonists, adenosine A[1] antagonists, neutral endopeptidase inhibitiors, dual-action ACE and neutral endopeptidase inhibitors.

These drugs belong to structurally diverse class of heterocyclics inlcuding substituted arylpiperazines. In this context, the 1-[4-Arylpiperazin-1-yl]-3-[2-oxopyrrolidin-1-1yl]propanes and 1-[4-Arylipiperazin-1-yl]-3-[2-oxopiperidin-1-yl]propanes of the formula 1 are structurally novel compounds and show significant antihypertensive and antischemic activities. Thus, these compounds would be useful in the treatment of hypertension and in preventing post-ischemic reperfusion injury (ischemia).

The most commonly used antihypertensive drugs are ACE's inhibitors (captopril and related drugs), $Ca_{++}$ channel blocker (nifedipine, verapamil, diltiazen) and peripheral $alpha_1$- adrengeric antagonist such as prazosin. As these drugs have one or the other side effects, there has been a continuous search for new and safe antihypertensive agents acting by these mechanism and by other novel mechanism which include mainly endothelin antagonists [Gulati, A. and Srimal, R. C. Drug Dev. Res., 26, 361, 1992; Antihypertensive Drugs. The Year's Drug News, 145–167, 1994].

There are no drugs available to prevent post-ischemic reperfusion inmury. However, the existing drugs or chemical agents like $Ca_{++}$ channel blockers [Hensch, G. Cardiovascular Res., 26, 14, 1992; Karin Pazyklenk, Robert A. Kloner. Cardiovascular Research, 26, 82, 1992], $K_{ATP}$ openers [Allen W. gomoll et al., J. Pharmacol. Exp. Ther., 281, 24, 1997; Arthur A. M. Wilde, Cardiovascular Research, 35, 181, 1997] $Na^+/H^+$ exchange inhibitors [Wolfgang Scholz et al., Cardiovas Res., 29, 260, 1995], have been shown to promote myocardial salvage and enhance function recovery in vivo, only hwen given before or during ischemic episode. However, administration of these agents only during reperfusion does not result in cardioprotective activity (Grover, G. J. et al., Cardiovasc. Drugs Ther., 4, 465, 1990 & Eur. J Pharmacol., 191, 11, 1990; Mizumura, T. et al., Circulation, 92, 1236, 1995). Besides the use of antiischemic agents in prevention of ischemic/reperfusion injury, there is an unmet medical need for agents to treat post-ischemic reperfusion injury which may simulate the real clinical situation of myocardial infarction.

PRIOR ART

Among a large number of the molecules incorporating arylpiperazines and showing antihypertensive activity, some relevant ones are thienopyrimidine-2,4-diones of formula 1 of the accompanying drawings—1 (U.S. Pat. No. 4,670,560, 1989), pyrazoles of formula 2 of the accompanying drawings—1 (Arya, V. P. et al., Experentia, 23, 514, 1967), tetrazoles of formula 3 of the accompanying drawings—1 (Hayae, S. et al. J. Med. Chem., 10, 400, 1967), prazocin analogs of formula 4 of the accompanying drawings—1 (Luther, R. R. et al., Am. Heart J., 117, 842, 1989; Ames, R. P. & Kiyasu, J. Y. J. Clin. Pharmacol., 29, 123, 1989), 2-[3-[4-(4-fluorophenyl)piperazin-1-yl]propanes]-1,4-benzothiazin-3(4H)-one of formula 5 of the accompany drawings—1 (Kajine, M. et al., Chem. Pharm. Bull., 39, 2885, 1991), uracil derivatives of formula 6 & 7 of the accompanying drawings—1 (Klmm, Von K. et al., Arzneim.

Forsch., 27, 1875, 1977), dihydropyridines of formula 8 of the accompanying drawings—1 (Suzuki, H. & Saruta, T. Cardiovasc. Drug Rev., 7, 25, 1989; Kubo, K. and Karasawa, A. 10$^{th}$ Int. Cong. Pharmacol., 146, 35, 1988; Kakihand, M. et al. Jpn. J. Pharmacol., 48, 223, 1988; Takenaka, T. et al., Arzneim. Forsch., 26, 2127, 1976; Kajimo, M. et al., Chem. Pharm. Bull., 37, 2225, 1989; Tricerri, S. Z. et al., U.S. Pat. No. 4,894,460, 1990: Chem. Abst., 113, 132218b, 1990), zolertine of formula 9 of the accompaning drawings—1 (Arya, V. P. et al., Experientia, 23, 514, 1967; Hayao, S. et al., J. Med. Chem., 10, 400, 1967), thiepin derivatives of formula 10 of the accompanying drawings—2 (Uno, H. et al., U.S. Pat. No. 4,749,703, 1988), triazolylamine of formula 11 of the accompanying drawings—1 (Mayer, W. E. et al., J. Med. Chem., 32, 593, 1989), aryloxypropanolamines of formula 12 of the accompanying drawings—2 (Ing, H. R. & Ormerod, W. E. J. Pharm. Pharmacol., 8, 666, 1956; Moran, N. C. and Perkins, M. E., Pharmacol. Exp. Ther., 124, 223m 1958), aryloxy/thioaryloxypropanes of formula 13 of the accompany drawings—2 (Agarwal, S. K. et al., Ind. J. Chem., 21B, 435, 1982; Ind. J. Chem., 21B, 914, 1982; Ind. J. Chem., 30B, 413, 1991, Rao, J. [3-[4-(4-fluorophenyl)piperazin-1-yl]propanes]-1,4-beuzothiazin-3(4H)-one of formula 5 of the accompanying drawings—1 (Kajine, M. et al. Chem. Pharm. Bull., 39, 2885, 1991), of formula 6 & 8 of the accompanying drawings—1 (Klmm, Von K. et al., Arzneim. Forsch., 27, 1875, 1977), dihydropyridines of formula 8 of the accompanying drawings—1 (Suzuki, H. & Saruta, T. Cardiovasc. Drug Rev., 7, 25, 1989; Kiibe, Karasawa, A. 10$^{th}$ Cong. Pharmacol., 734, 1987; Drugs of the Future, 14, 291, 1989; Meguro, K. et al., Chem. Pharm. Bull., 33, 3787, 1985; Nakaya, H. et al., Eur. J. Pharmacol., 146, 35, 1988; Kakihand, M. et al., Jpn. J. Pharmacol., 48, 223, 1988; Takenaka, T. et al., Arzneim. Forsch., 26, 2127, 1976; Kajimo, M. et al. Chem. Pharm. Bull., 37, 2225, 1989; Tricerri, S. Z. et al., U.S. Pat. No. 4,894,460, 1990 Chem. Abst., 113, 132218b, 1990), zolertine of formula 10 of the accompaning drawings—1 (Arya, V. P. et al., Experientia, 23, 514, 1967; Hayao, S. et al., J. Med. Chew. 10, 400, 1967), thiepin derivatives of formula 10 of the accompanying drawings—2 (Uno, H. et al., U.S. Pat. No. 4,749,703, 1988), triazolylamine of formula 11 of the accompanying drawings—1 (Mayer, W. E. et al., J. Med. Chew., 32, 593, 1989), aryloxypropanolamines of formula 12 of the accompanying drawings—2 (lug, H. R. & Ormerod, W. E., J. Pharm. Pharinacol., 4, 21, 1952; Petrow, V. et al., J. Pharm. Pharmacol., 8, 666, 1956; Moran, N. C. and Perkins, M. E., Pharmacol. Exp. Ther., 124, 223, 1958), aryloxy/thioaryloxy arylpiperazinylpropanes of formula 13 of the accompanying drawings—2 (Agarwal, S. K. et al., Ind. J. Chem., 21B, 435, 1982; Ind. J. Chem., 21B, 914, 1982; Ind. J. Chem., 30B, 413, 1991; Rao, J. et al., In. J. Chem., 26B, 761, 1987; Saxena, A. K. et al., Ind. J. Chem., 32B, 1249, 993) quinolylethanes of formula 14 of the accompanying drawings—2.(Murti, A. et al. Ind. J. Chem., 28B, 934 1989), trimetazidine of formula 15 of the drawing—2 (Fujita, Y., Jpn. J. Pharmacol. 17, 19, 1976), lidoflazine of formula 16 of the drawing—2 (Daenen, W. & Flameng, W., Angiology, 32, 543, 1981), isoquinoline derivatives of formula 17 of the accompanying drawings—2 (Nakajiza, T. et al., Arzneirn-Forsch., 37, 674, 127) dihydropyridazinone derivative of formula 18 of the accompanying drawings—2 (Yao, F. M. et al., Yaaxue Xuebao, 28, 548, 199!3), pyrroloquinoline derivative of formula 19 of the accompanying drawings—2 (Jasserand, D. et al., Ger. Often. DE 4,128,015, 1993: Chem. Abstr., 119, 139255f, 1993).

SUMMARY OF THE INVENTION

The invention relates to a process for the synthesis of a propane compound of formula 1:

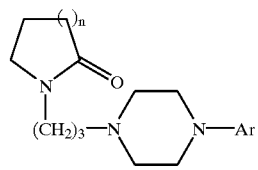

wherein Ar represents a phenyl ring substituted with halogen, alkoxy, alkyl or heteroaryl, n=1 or n=2 and said compounds having use as therapeutic agents for hypertension, ischemic cardiovascular and other adrenergic receptors related disorders, said process including condensing a 2-pyrrolidone of formula 2 (n=1) or a 2-piperidone of formula 2 (n=2) with a 1-[4-substituted arylpiperazin-1-yl]-3-chloropropane of formula 5, where Ar represents a phenyl ring substituted with halogen, alkoxy, alkyl or heteroaryl in the presence of a base and an organic solvent at a temperature ranging from about 120–150° C. for a period varying between about 90 min. to 14 hrs. to produce a corresponding 1-[4-substituted arylpiperazin-1-yl]-3-[2-oxopyrrolidin/piperidin-1-yl]propane of formula 1.

In a preferred embodiment, the propane compound synthesized includes at least one of:

(a) 1-[4-(3-chlorophenyl)piperazin-1-yl]-3-[2-oxopyrrolidin-1-yl]propane;

(b) 1-[4-(4-chlorophenyl)piperazin-1-yl]-3-[2-oxopyrrolidin-1-yl]propane;

(c) 1-[4-(3-fluorophenyl)piperazin-1-yl]-3-[2-oxopyrrolidin-1-yl]propane;

(d) 1-[4-(4-fluorophenyl)piperazin-1-yl]-3-[2-oxopyrrolidin-1-yl]propane;

(e) 1-[4-(4-ethylphenyl)piperazin-1-yl]-3-[2-oxopyrrolidin-1-yl]propane;

(f) 1-[4-(2-ethylphenyl)piperazin-1-yl]-3-[2-oxopyrrolidin-1-yl]propane;

(g) 1-[4-(4-chlorophenyl)piperazin-1-yl]-3-[2-oxopiperidin-1-yl]propane;

(h) 1-[4-(3-chlorophenyl)piperazin-1-yl]-3-[2-oxopiperidin-1-yl]propane;

(i) 1-[4-(4-fluorophenyl)piperazin-1-yl]-3-[2-oxopiperidin-1-yl]propane;

(j) 1-[4-(2-ethylphenyl)piperazin-1-yl]-3-[2-oxopiperidin-1-yl]propane;

(k) 1-[4-(2-methoxyphenyl)piperazin-1-yl]-3-[2-oxopiperidin-1-yl]propane;

(l) 1-[4-(2-pyridyl)piperazin-1-yl]-3-[2-oxopiperidin-1-yl]propane; and (m) 1-[4-(3-trifluoromethylphenyl)piperazin-1-yl]-3-[2-oxopiperidin-1-yl]propane.

In another embodiment of the process, the halogen is selected from the group consisting of chlorine, fluorine, bromine, and iodine, and mixtures thereof, the alkoxy is selected to be a $C_1$–$C_{10}$oxy, the alkyl is selected to be $C_1$–$C_{10}$alkyl, and the heteroaryl is selected to be a $C_4$–$C_{10}$heteroaryl. In another embodiment, the molar ratio of the compounds of formula 2 and 5 is about 1:1. In another embodiment, the solvent is selected from toluene or xylene or mixtures thereof, and the amount of the solvent comprises from about 5 to 6 ml solvent per mmol of the reacting compounds of formula 2 and 5. In yet another embodiment, the atomic/molar ratio of the base sodium/potassium metal or potassium tert. butoxide to the compounds of formula 2 and 5 is about 1:1.

The invention also relates to a pharmaceutical composition including a compound of formula I in admixture with a pharmaceutically acceptable conventional carrier.

The invention also relates to a process for preparing a pharmaceutical composition which includes bringing a compound of the formula I above into association with a pharmaceutically acceptable carrier.

The invention further relates to a method of treating hypertension in mammals that comprises administering to a subject in need thereof an effective amount of a compound of formula I above. The invention further relates to a method of treating peripheral vascular diseases in mammals that comprises administering to a subject in need thereof an effective amount of a compound of formula I above. In another embodiment, the invention relates to a method of antagonizing peripheral alpha-adrenergic receptors in mammals that comprises administering to a subject in need thereof an effective amount of a compound of formula I. The invention further relates to a method of treating diseases arising out of alterations in central circulations, peripheral circulations, or adrenergic receptor systems that comprises administering to a subject in need thereof an effective amount of a compound of formula I. The invention further relates to a method of treating reperfusion injury in mammals that comprises administering to a subject in need thereof an effective amount of a compound of formula I above. The invention also relates to a method of treating ischemic diseases in mammals that comprises administering to a subject in need thereof an effective amount of a compound of formula I.

In one preferred embodiment, the diseases to be treated are selected to be myocardial ischemia, myocardial infarction (MI), angina pectoris, cardiac surgical intervention, renal ischemia, circulatory insufficiency in extremities, stroke, trauma, or a combination thereof. In another preferred embodiment, the ischemic diseases are selected to be myocardial infarction (MI), angina pectoris, cardiac surgical intervention, or a combination thereof.

BRIEF DESCRIPTION OF THE DRAWINGS

The present invention may be more clearly understood by reference to the following Figures.

DETAILED DESCRIPTION OF THE INVENTION

Figure 1:
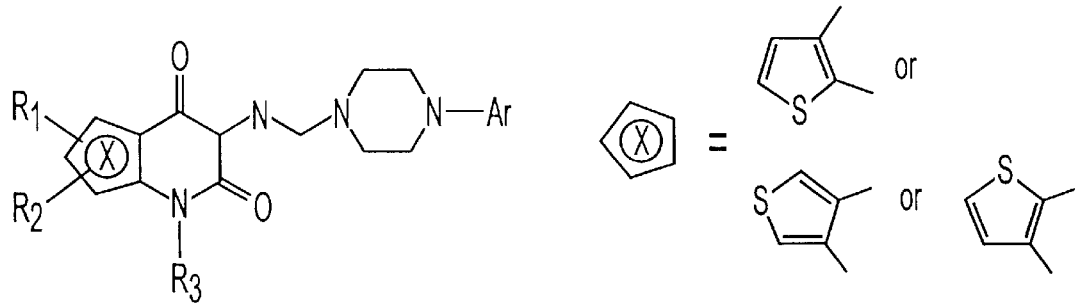
FIG. 1 illustrates prior art thienopyrimidine-2-,4-dione compounds of formula 1.
Figure 2:
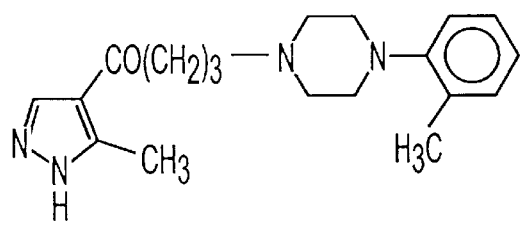
FIG. 2 illustrates prior art pyrazole compounds of formula 2.
Figure 3:
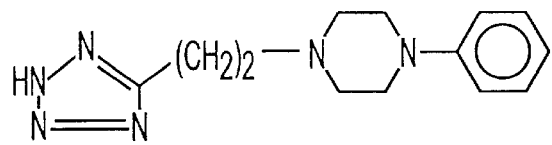
FIG. 3 illustrates prior art tetrazole compounds of formula 3.
Figure 4:
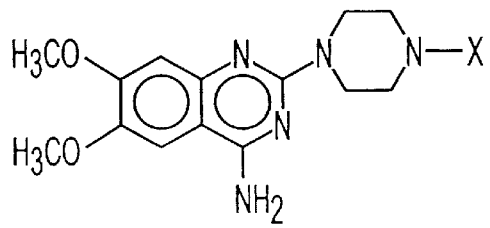
FIG. 4 illustrates prior art prazocin analog compounds of formula 4.
Figure 5:
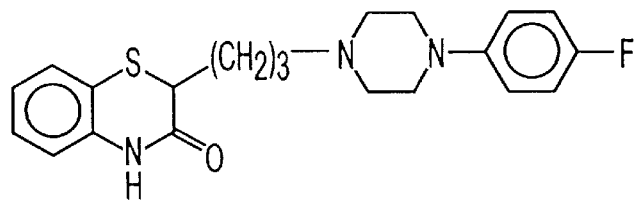
FIG. 5 illustrates prior art 2-[3-[4-(4-fluorophenyl)piperzin-1-yl]propanes]-1,4-benzothiazin-3(4H)-one compounds of formula 5.
Figure 6:
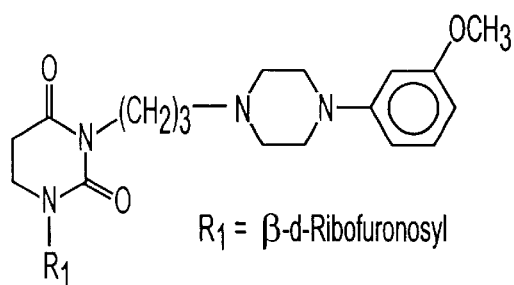
FIGS. 6 and 7 illustrate prior art uracil compounds of formulas 6 and 7.
Figure 7:
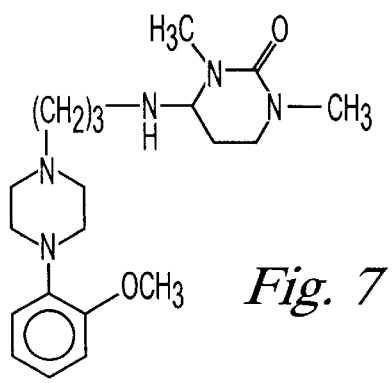
Figure 8:
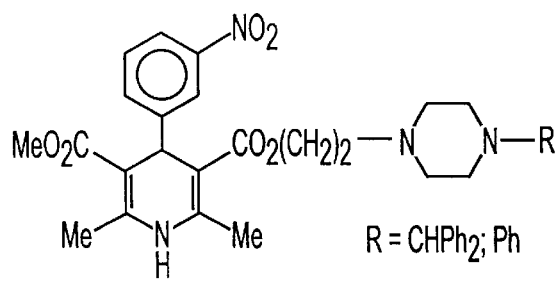
FIG. 8 illustrates prior art dihydropyridine compounds of formula 8
Figure 9:
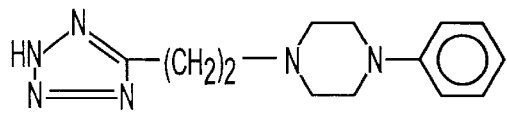
FIG. 9 illustrates prior art zolertine compounds of formula 9
Figure 10:
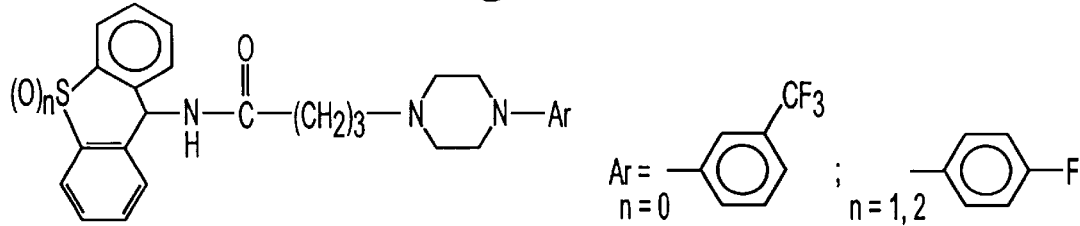
FIG. 10 illustrates prior art thiepin compounds of formula 10.
Figure 11:
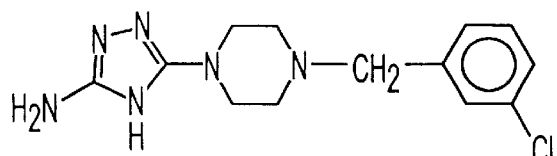
FIG. 11 illustrates prior art triazolylamine compounds of formula 11.
Figure 12:
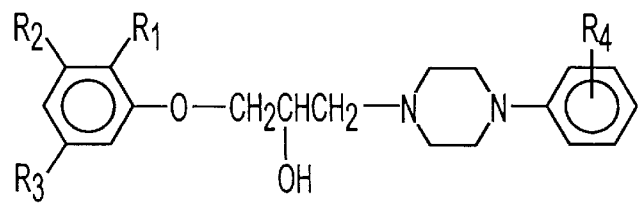
FIG. 12 illustrates prior art aryloxypropanolamine compounds of formula 12.
Figure 13:
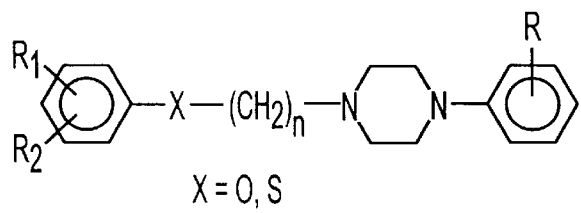
FIG. 13 illustrates prior art aryloxy and thioaryloxy arylpiperazinylpropane compounds of formula 13.
Figure 14:
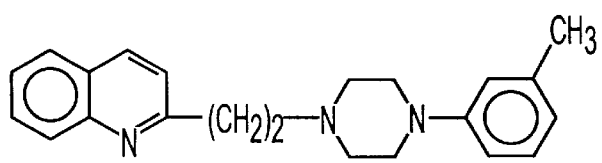
FIG. 14 illustrates prior art quinolylethane compounds of formula 14.
Figure 15:
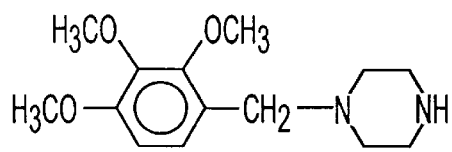
FIG. 15 illustrates prior art trimetazidine compounds of formula 15.
Figure 16:
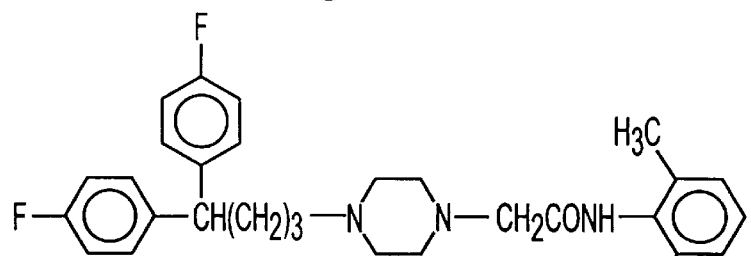
FIG. 16 illustrates prior art lidoflazine compounds of formula 16.
Figure 17:
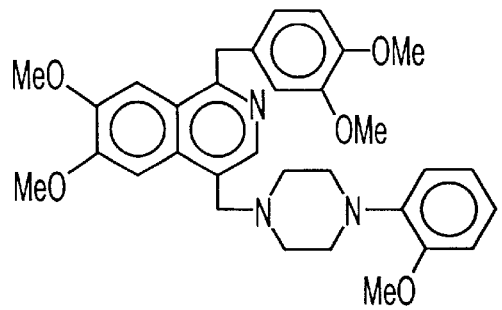
FIG. 17 illustrates prior art isoquinolylmethyl compounds of formula 17.
Figure 18:
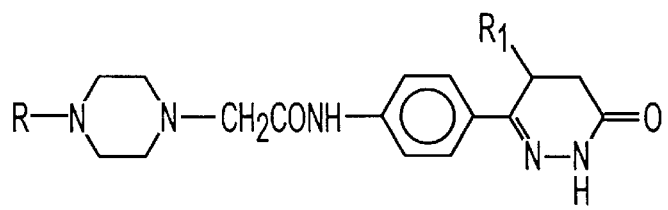
FIG. 18 illustrates prior art dihydropyridazinone derivative compounds of formula 18
Figure 19:
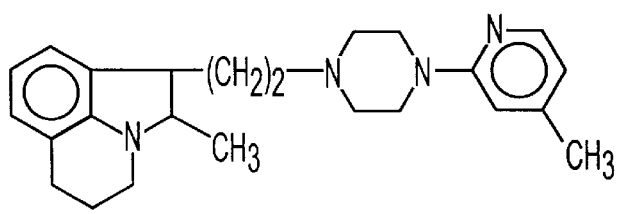
FIG. 19 illustrates prior art pyrroloquinoline derivative compounds of formula 19.
Figure 20:
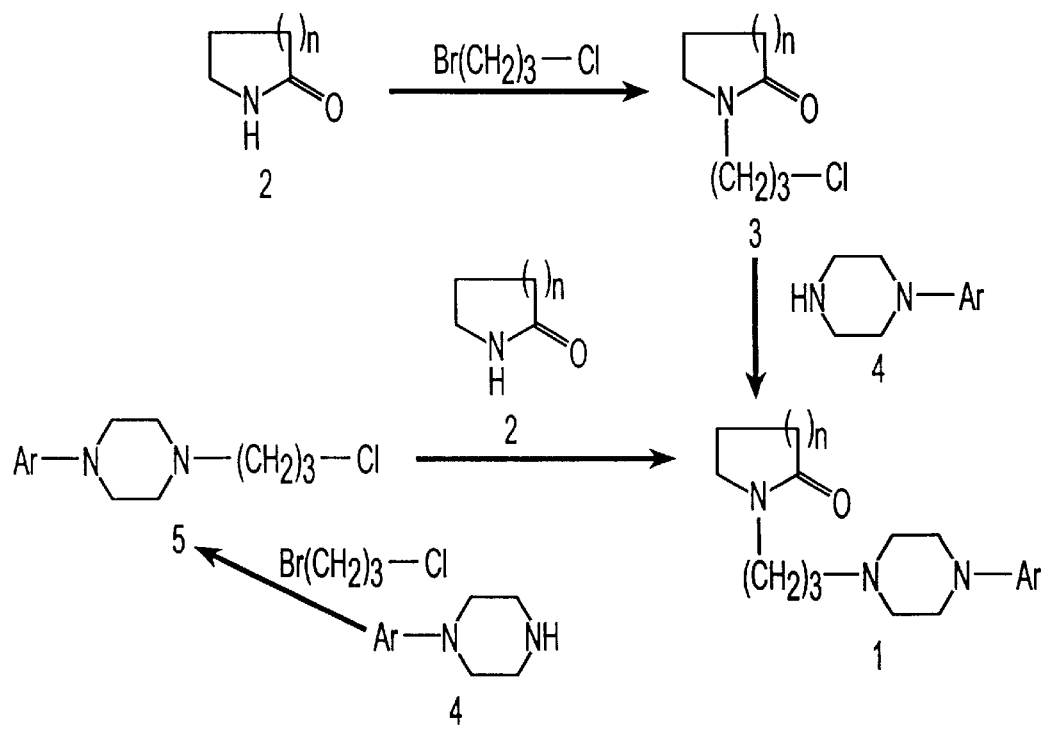
FIG. 20 illustrates the reaction sequence resulting in 1-[4-ARYLPIPERAZIN-1-YL]-3-[2-OXOPYRROLIDIN-1-YL] PROPANES and 1-[4-ARYLPIPERAZIN-1-YL]-3-[2-OXOPIPERIDIN-1-YL] PROPANES according to the present invention.

The invention is mainly centered around the following objects: (1) The first object of the invention is to provide a Process for preparing novel molecules incorporating piperazine flanked on one side by aromatic system and on the other side by 2-(oxopyrrolidin-1-yl)propanes or 2-(oxopiperidin-1-yl)propanes that exhibit better therapeutic efficicacy to treat hypertension over the existing antihpertensive agents. (2) The second object of the invention is to provide a process for preparing novel 1-(4-arylpiperazin-1-yl)-3-(2-oxopyrrolidin-1-yl)propanes and 1-(4-arylpiperazin-1-yl)3-(2-oxopiperidin-1-yl)propanes exhibiting activity against ischemic reperfusion injury for which there is no agent available till date to the best of our knowledge. (3) The third object of the invention is to provide 1-(4-arlipiperazin-1-yl)-3-(2-oxopyrrolidin-1-yl)propanes and 1-(4-arylpiperazin-1-yl)-3-(2-oxopiperidin-1-yl)propanes as therapeutic agents for the diseases arising out of alterations/impairment in central/peripheral circulations and adrenergic receptors systems, such as myocardial ischemia, myoccardial infarction (MI), angina pectoris, any cardiac surgical interventions, renal ischemica, circulatory insufficiency in extremities, stroke and trauma.

This invention is concerned with novel pharmacologically active substances and relates to new 1-(4-arylpiperazin-1-yl)-3-(2-oxopyrrolidin-1yl)propanes and 1-(4-arylpiperazin-1-yl)-3-(2-oxopiperidin-1-yl)propanes as potential therapeutic agents for hypertension ischemia, cardiovascular and other adrenergic receptors related disorders.

Accordingly, this invention provides a process for preparing compounds of the formula 1 which are used as potential theraputic agents for hypertension, ischemia

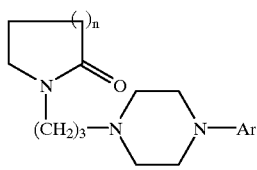

cardiovascular and other adrenergic receptors related disorders, wherein Ar represents a phenyl ring substituted by the groups like halo, alkoxy, alkyl or heteroryl, n=1 or n=2. Therefore, the present invention provides a process for the syntheses of compounds of formula 1 which formula is shown above, wherein Ar represents a heteroaryl ring or a phenyl ring substituted with a halogen, alkoxy, alkyl or heteroaryl, n=1 or n=2, said process comprising condensing 2-pyrrolidone of formula 2(n=1) or 2-piperridone of formula 2 (n=2) with 1-[4-substituted arylpiperazin-1yl]-3-chloropropanes of formula 5 where Ar represents a phenyl ring substituted by the group like halo, alkoxy, alkyl or heteroaryl in the presence of a base and organic solvent at a temperature ranging from 120–150° C. for a period varying between 90 min. to 14 hrs. to produce the corresponding 1-[4-substituted arylpoperazin-1-yl]-3-[2-oxopyrrolidin/piperidin-1-yl]propanes of formula 1 (fomulae 1 to 5 are shown in scheme 1 of the accompanying drawings). The preferred compound of formula 1 are shown herebelow (a) 1-[4-(3-chlorophenyl)piperazin-1-yl]-3-[2-oxopyrrolidin-1-yl]propane.

(b) 1-[4-(4-chlorophenyl)piperazin-1-yl]-3-[2-oxopyrrolidin-1-yl]propane.

(c) 1-[4-3-fluorophenyl)piperazin-1-yl]-3-[2-oxopyrrolidin-1-yl]propane.

(d) 1-[4-(4-fluorophenyl)piperazin-1-yl]-3-[2-oxopyrrolidin-1-yl]propane.

(e) 1-[4-(4-fluorophenyl)piperazin-1-yl]-3-[2-oxopyrrolidin-1-yl]propane.

(f) 1-[4-(2-ethylphenyl)piperazin-1yl]-3-[2-oxopyrrolidin-1-yl]propane (g) 1-[4-(4-chlorophenyl)piperazin-1-yl]-3-[2-oxopiperidin-1-yl]propane.

(h) 1-[4-(3-chlorophenyl)piperazin-1-yl]-3-[2-oxopiperidin-1-yl]propane.

(i) 1-[4-(4-fluorophenyl)piperazin-1-yl]-3-[2-oxopiperidin-1-yl]propane.

(j) 1-[4-(2-ethylphenyll)piperazin-1-yl]-3-[2-oxopiperidin-1-yl]propane.

(k) 1-[4-(2-methoxyphenyl)piperazin-1-yl]-3-[2-oxopiperidin-1-yl propane.

(l) 1-[4-(2-pyridyl)piperazin-1-yl]-3-[2-oxopiperidin-i-yl]propane.

(m) 1-[4-(3-trifluoromethylphenyl)piperazin-1-yl]-3-[2-oxopiperidin-1-ylI propane.

In the specification and claims, the compounds with n=1 designates 2-oxopyrrolidin-1-yl while with n=2, 2-oxopiperidin-1-yl groups. Aryl designates a pyridyl or phenyl, or a phenyl group substituted by one or more alkyl, alkoxy or halogen groups.

A preferred group of compound comprises those in which n=1 or n=2, aryl group is 2 or 4-pyridyl, phenyl, or phenyl group substituted by alkyl groups like H, $C_2H_5$, $CF_3$, alkoxy like methoxy, halo like chloro, fluoro etc. The compounds of this invention have useful biological activities and have in particular strong antihypertensive and antiischemic activities.

DESCRIPTION OF PREFERRED EMBODIMENTS

The general reaction sequence leading to 1-[4-arylpiperazin-1-yl]-3-[2-oxopyrrolidin-1-yl]propanes or 1-[4-arylpiperazin-1-yl]3-[2-oxopiperidin-1-yl]propanes is shown in scheme 1 of the accompanying drawings.

It will be noted that according to the foregoing schemes there are two general methods leading to the synthesis of 1. In the first general method the 2-pyrrolidone (2, n=1) or 2-piperidone (2, n=2) is condensed with 1-bromo-3-chloropropane in presence of bases selected from potassium tert. butoxide, pulvarised alkali metals selected from sodium or potassium in nonpolar solvents selected from benzene, xylene, toluene at a temperature ranging from 110 to 150° C. for 1.15 to 14 hrs to give 1-chloro-3-[2-oxo-pyrrolidin-1-yl]propane (3, n=1) or 1-chloro-3-[U-oxo-piperidin-1-yl]propane (3, n=2) which on condensation with appropriately substituted piperazines, gave the required compounds of formula 1. This reaction may be carried out in solvents selected from acetone, methylethyl ketone, tetrahydrofuran or dimethylformamide using bases selected from triethylamine, pyridine, sodium or potassium carbonate and catalysts selected from sodium/potassium iodide to improve the yield of the compounds of formula 1 and the said method is the subject matter of the copending U.S. application Ser. No. 08/960,335.

According to the method, the substituted piperazine (4) was condensed with 1-bromo-3-chloropropane in presence (of bases selected from sodium or potassium carbonate and catalytic amounts of sodium or potassium iodide in solvents selected from DMF, toluene, xylene etc. at a temperature ranging from 70 to 150° C. for 8 to 14 hrs to give 1-chlro-3-(4-substituted piperazin-1 yl)propane (5) which on condensation with 2-oxo-pyrrolidine or 2-oxopiperidine in presence of bases selected from potassium tert. butoxide or pulverised sodium or potassium in nonpolar solvents selected from xylene, toluene at a temperature ranging from 110 to 150° C. for 1.15 to 14 hrs yield the required compounds of formula 1.

The 1-[4-arylpiperazin-1-yl]-3-[2-oxopyrrolidin-1-yl]propanes (1 n=1) and 1-[4-arylpiperazin-1-yl]-3-[2-oxopiperidin-1-yl]propanes (1 n=2) in free form can, if desired be converted in to their non-toxic pharmaceutically acceptable acid addition and quaternary ammonium salts. Salts which may be formed comprise, for example, salts with inorganic acids such as hydrochloride, hydrobromide, hydroiodide, sulphate and phosphate. They may also comprise salts with organic acids including mono basic acids such as acetate or propionate and especially those with hydroxy organic acids and dibasic acids such as the citrate, tartarate, malate and maleate. Among useful quaternary ammonium salts are those formed by such alkyl halides as methyl iodine and n-hexyl bromide.

The compounds of the invention show marked antihypertensive alpha-adrenergic blocking and antiischemic activities and can he used as therapeutic agents in diseases arising out of alterations/impairment in central/peripheral circulations and adrenergic receptors systems, such as myocardial ischemia, myocardial infarction (MI), angina pectoris, any cardiac surgical interventions, renal ischemia, circulatory insufficiency in extremities, stroke and trauma as shown for instance by the following data of the compound 1-[4-(4-fluorophenyl)piperazin-1-yl]-3-[2-oxopyrro-lidin-1-yl]propane.

Pharmacological activity
1. Acute toxicity ($LD_{50}$)
   Mice 147.0 mg/kg i.p. (C.L.=85.3–253)
   562.0 mg/kg p.o. (C.L.=383–825)
2. Effect on blood pressure, heart rate and adrenaline vasopressor response of anaesthetized (pentobarbitone sodium 40 & 60 mg/kg i.p. in cat and rat respectively) normotensive & hypertensive rat & cat model preparations.

| Dose (uMol/kg i.d.) | B.P. Fall (%) | Dur. (min.) | Heart rate Pre/post treatment | Adrenaline vasopressure response % inhibition | No. of exp. |
|---|---|---|---|---|---|
| (A) CAT | | | | | |
| (i) Naturally occurring hypertensive cat | | | | | |
| 10 | 16 | 110 | 195/195 | 49 | n = 4 |
| 20 | 22 | >156.75 | 177/185 | R26 | n = 4 |
| (ii) Normotensive cat | | | | | |
| 10 | 22 | 85 | 200/170 | 26 | n = 4 |
| 20 | 21 | >102.5 | 185/165 | 34.75 | n = 4 |

| Dose (uMol/kg i.d.) | B.P. Fall (%) | Dur. (min.) | Heart rate Pre/post treatment | Adrenaline vasopressure response % inhibition | No. of exp. |
|---|---|---|---|---|---|
| (B) RAT | | | | | |
| (i) Hypertensive rat model preparation | | | | | |
| 5 | 27 | 51 | 350/370 | 33 | n = 3 |
| 10 | 22 | 76 | 356/340 | 23 | n = 5 |
| 20 | 29 | 100 | 310/275 | 54 | n = 1 |
| (ii) Normotensive rat model preparation | | | | | |
| 2 i.v. | 25 | 11 | 350/370 | +7 R22 | n = 2 |
| 10 i.v. | 10 | 3 | 315/360 | +14 R 28 | n = 2 |
| 20 i.v. | 21 | 27.5 | 315/285 | −9.5 R 42 | n = 2 | i.d. = Intraduodenal route; R = Reversal

3. Possible site and mechanism of action

(I) SITE

| | Dose (umol/kg i.d.) | B.P. fall (%) | Dur. (min.) |
|---|---|---|---|
| (i) Spinal transected cat | 2–10 | 14–18 | 15–30 |
| (ifi) ICV | 0.34–1.36 | 8–10 | 10–15 |
| (iii) Rat hind limb perfusion | | | |
| | Total dose (ug) | Percent change in flow | |
| | 10 | no effect | |
| | 25 | +35 (Vasodilation) | |
| | 50 | +50 (Vasodilation) | |

(II) MECHANISM OF ACTION
(A) In vitro
(i) Isolated aortic strip:
  Endothelin induced contraction was inhibited significantly.
  Even after washing the preparation endothelin caused relaxation rather than contraction.
(ii) Isolated Guinea pig ileum preparation endothelin relaxation rather than contraction.

Compound showed significant antihistaminic activity (0.5–5.0 ug/ml).
(iii) Langendorffs perfused rat heart preparation:
  Lower dose of this compound (1 ug) showed some negative chronotropic effect (30% for 10 min.) but higher doses (3–5 ug) showed less negative chronotropic effect (26 & 5% for 14 & 5 min. respectively).
(iv) Konzett and Rossler preparation:
  Compound showed some antihistaminic activity against histamine induced bronchoconstriction.
(v) Rat aortic ring preparation:
  NE induced contraction was inhibited by the compound.
(B) In viva Drug antagonism studies at 2 uMol dose i.v. in cat:
  (i) Pretreatment with $alpha_1$-adrenergic receptor blocker, prazosin significantly (90%) reduced antihypertensive effect.
  (ii) Pretreatment with Ca++ channel blocker, verapamil significantly reduced antihypertensive effect (50%).
  (iii) Pretreatment with captopril (an ACE inhibitor) or Dup- 753 (an angiotension II-receptor antagonist) also reduced the antihypertensive effect (33%)
  (iv) ATP sensitive potassium channel (KATP) blocker glibenclamide pretreatment only partially reduced the fall in LiHOI pressure.
  (v) Pretreatrnent with, atropine sulphate, mepyramine maleate, propranolol, or yohimbine failed to alter the antihypertensive effect of this compound.
(4) Comparative antihypertensive effect with clinically used antihypertensive drugs at 2 uMol/kg i.v. dose in cat

| | Drug | B.P. fall (%) | Dur. (Min.) |
|---|---|---|---|
| (i) | Verapamil | 55 | 22 |
| (ii) | Captopril | 14 | 28 |
| (ii) | Compound 1 of formula 1 | 22 | 25 |

Ar = $C_6H_4$-4-F, where n = 1

(5) Cardioprotective activity
The most interesting observation is its cardioprotective effect against myocardial stunning at a much smaller dose than antihypertensive dose. Further, in Langendorff perfused rat heart preparation subjected to even upto 90 mm. global ischemia, the compound at 0.001 ug/ml conc. given at the time of reperfusion revived normal rhythmic contraction started within 2 mm. (Table 1) and incidence of reperfusion induced arrhythmia were abolished.

TABLE 1

Compound administered at the time of reperfusion at the dose of 0.001 ug/ml on prolong period (90 min.) of ischemic insult.

| | | | Percentage recovery | |
|---|---|---|---|---|
| S. No. | Compound | Onset (min.) | 15 min. | 30 min. |
| 1. | Control[a] | 3 | 0.5 | 17.5 |
| 2. | Compound 1 of formula 1, where Ar = C6H4-4-F, n = 1 | 4 | 81.25 | 87.15 |
| 3. | Nifedipine[a] ($10^{-6}$ M) | 2.5 | 0.66 | 0.0 |

[a]Ischemic insult (45 mm.)

Comparable results for hypotensive/antihypertensive and antiischemic activities were obtained with a number of other compounds of formula I (Table 2 & 3).

TABLE 2

Effect on blood pressure, heart rate and adrenaline vasopressure response at anaesthetized (pentobarbitone sodium 35 mg/kg (iv) cat

| Compound of formula 1 Ar | n | Dose (umol/kg i.v.) | B.P. fall % | Dur. (min.) | Adrenaline[a] vasopressure response % inhibition |
|---|---|---|---|---|---|
| $C_6H_4$-4F | 1 | 2.0 | 25 | 71 | 9 |
|  |  | 10.0 | 31 | >112 | R |
| $C_6H_4$-2-$C_2H_5$ | 1 | 2.0 | 13 | 10 | Pt |
|  |  | 10.0 | 62 | 10 | — |
| $C_6H_4$-3-Cl | 1 | 2.0 | 25 | 20 | Pt– |
|  |  | 10.0 | 55 | >57 |  |
| $C_6H_4$-3F | 1 | 2.0 | 18 | 3 | 80 |
|  |  | 10.0 | 32 | 30 | R |
| $C_6H_4$-2-$OCH_3$ | 1 | 2.0 | 19 | 19 | 47 |
|  |  | 10.0 | 23 | 67 | R |
| 2-Pyridyl | 1 | 2.0 | 22 | 16 | 40 |
|  |  | 10.0 | 40 | 43 | Pt |
| 2-Pyridyl | 2 | 2.0 | 34 | 53 | 28 |
|  |  | 10.0 | 42 | >71 | Pt |
| $C_6H_4$-4-Cl | 2 | 2.0 | 24 | 20 | 20 |
|  |  | 10.0 | 46 | 25 | 25 |
| $C_6H_4$-3-Cl | 2 | 2.0 | 27 | 9 | 33 |
|  |  | 10.0 | 44 | 62 | 10 |
| $C_6H_4$-3-$CF_3$ | 2 | 2.0 | — | — | Pt |
|  |  | 10.0 | 10 | Tr | 25 |
| $C_6H_4$-2-$C_3H_5$ | 2 | 2.0 | 35 | 55 | 68 |
|  |  | 10.0 | 20 | 63 | R |
| $C_6H_4$-4-F | 2 | 2.0 | 23 | 40 | 46 |
|  |  | 10.0 | 33 | >84 | R |

[a]R = Reversal; Pt = potentiation (was within 20%)

TABLE 3

Compound administered at the time of reperfusion at a dose of 0.001 ug/ml on brief period (16 min.) of ischemic insult.

| Compound of formula 1 |  | Onset | Percentage recovery | |
|---|---|---|---|---|
| Ar | n | (min.) | 15 min. | 30 min. |
| Control | — | 2.0 | 104.50 | 118.10[a] |
| $C_6H_4$-4-F | 1 | 1.5 | 81.25 | 78.12 |
| $C_6H_4$-2-$C_2H_5$ | 1 | 3.0 | 106.06 | 136.36 |
| $C_6H_4$-3-Cl | 1 | 1.0 | 50.00 | 88.80 |
| $C_6H_4$-4-$C_2H_5$ | 1 | 2.0 | 103.03 | 60.60 |
| $C_6H_4$-3-F | 1 | 2.0 | 120.00 | 180.00 |
| $C_6H_4$-3-Cl | 1 | 3.0 | 31.50 | 39.40 |
| $C_6H_4$-2-$OCH_3$ | 1 | 2.0 | 45.40 | 59.09 |
| $C_6H_4$-4-Cl | 1 | 1.0 | 87.50 | 120.80 |
| 2-Pyridyl | 1 | 2.0 | 47.60 | 71.40 |

[a]Arrhythmia present

The following examples are provided by the way of illustration of the present invention and should in noway be construed as a limitation thereof including the linker (propyl) between pyrrolidone/piperidone and N-arylpiperazine which may be ethyl or butyl.

EXAMPLE 1

(a) Preparation of 1-chloro-3-[2-oxopyrrolidin-1-yl] propane (i) A mixture of 2-pyrrolidone (1 g, 12.0 mmol) and finely pulverized sodium metal (0.28 g, 12.0 mmol) in dry xylene (60 ml) was heated at 110° C. with vigrous stirring, 1-bromo-3-chloropropane (1.8 g, 12.0 mmol) was added to the stirred reaction mixture after 3 hours and the heating at 110° C. was continued for 6 hours. The reaction mixture was filtered and xylene was removed under reduced pressure. The residue was distilled under reduced pressure to give 3 (n=1), B.P. 145° C/1 mm., yield 1.52 g (80%). IR (Neat) 2980, 2880, 1710, 14W), 1420, 1280, 1050. $^1$H NMR ($CDCl_3$): 1.92–2.18(m, 4H, 4' & 2-$CH_2$), 2.40(t, 2H, J=6.0 Hz, 3'-$CH_2$), 3.42(t, 4H, J=6.0 Hz, 5' & 3-$CH_2$), 3.58(t, 2H, J=6.0 Hz, 1-$CH_2$).

MS: m/z 161 (M+).

Mol. formula $C_7H_{12}NOCl$: Found: C, 51.96; H, 7.48; N, 8.61 Calcd.: C, 52.11; H, 7.45; N,8.69%.

(ii) A mixture of 2-pyrrolidone (10 g, 120.0 mmol) and finely pulverized sodium metal (2.76 g, 120.0 mmol) in dry xylene (600 ml) was heated at 150° C. with vigrous stirring. 1-Bromo-3-chloropropane (18.84 g, 120.0 mmol) was added to the stirred reaction mixture after 30 minutes and the heating at 150° C. was continued for 1 hour. The reaction mixture was filtered and xylene was removed under reduced pressure. The residue was distilled under reduced pressure to give 3 (n=1), B.P. 145° C./1 mm., yield 16.09 g (85%).

(iii) A mixture of 2-pyrrolidone (2 g, 23.0 mmol) and finely pulverized sodium metal (0.529 g, 23.0 mmol) in dry toluene (120 ml) was heated at 120° C. with vigrous stirring. 1-Bromo-3-chloropropane (3.97 g, 25.0 mmol) was added to the stirred reaction mixture after 6–7 hours and the heating at 120° C. was continued for 7 hours. The reaction mixture was filtered and toluene was removed under reduced pressure. The residue was distilled under reduced pressure to give the compound 3 (), B.P. 145° C./1 mm., yield 2.86 g (75%).

(iv) A mixture of 2-pyrrolidone (1 g, 12.0 mmol) and finely pulverized potassium metal (0.47 g, 12.0 mmcl) in dry xyleiie (60 ml) was heated at 150° C. with vigrous stirring. 1-P,rumo-3-chloropropane (1.8 g, 12.0 mmol) was added to the stirred reaction mixture after 20 minutes and the heating at 150° C. was continued for 1 hour. The reaction mixture was filtered and xylene was removed under reduced pressure. The residue was distilled under reduced pressure to give 3 (n=1), B.P. 145 CC/i mm., yield 1.43 g (75%).

(v) A mixture of 2-pyrrolidone (1 g, 12.0 mmol) and pot<1 s~1 um tert. butoxide (1.34 g, 12.0 mmcl) in dry xylene (60 ml) was heated at 150° C. with vigrous stirring. 1-Bromo-3-chloropropalle (1.8 g, 12.0 mmcl) was added to the stirred reaction mixture after 2 hours and the heating at 150° C. was continued for 3 hours. The reaction mixture was filtered and xylene was removed under reduced pressure. The residue was distilled under reduced pressure to give 3 (n=1), B.P. 145° C./1 mm., yield 1.24 g (65%).

(b) Preparation of 1-chloro-3-(2-oxopiperidin-1-yl) propane

A mixture of 2-piperidone (1.19 g, 12.0 mmcl) and fnely pulverized sodium metal (0.28 g, 12.0 mmol) in dry xylene (70 ml) was heated at 110° C. with vigrous stirring, 1-bromo-3-chloropropane (1.89 g, 12.0 mmol) was added to the stirred reaction mixture after 3 hours and the heating at 110° C. was continued for 6 hours. The reaction mixture was filtered and xylene was removed under reduced pressure. The residue was chromatographed on silica gel usinq hexane and chloroform as eluant to get 3 (n=2), B.P. 91° C./0.01 mm., yield 1.33 g (63.33%). IR (Neat): 3862, 3298, 2950, 2474, 2324, 1640, 1478, 1432, 1336, 1184, 1096, 754. $^1$H NMR (CDCl$_3$): 1.79–2.36(m, 8H), 3.15–3.67(m,6H). MS: m/z 175 (M+).

Mol. formula C$_8$H$_{14}$NOCl: Found: C, 54.90; H, 8.28; N, 8.25 Calcd.: C, 54.69; H, 8.03; N, 7.97%.

EXAMPLE 2

(a) Preparation of 1-[4-(3-chlorophenyl)piperazin-1-yl]-3-[2-oxopyrrolidin-1-yl]propane of the formula 1, where Ar=C$_6$H$_4$-3-Cl, n=1

A mixture of 1-chloro-3-[2-oxopyrrolidin-1-yl]propane (1 g, 6.2 mmol),, 1-(3-chlorophenyl)piperazine (1.22 g, 6.2 mmol) anhydrous Na$_2$CO$_3$ (0.33 g, 3.1 mmol) and NaI (0.093 g, 0.6 mmol) in dry DMF (5 ml) was stirred at 70° C. for 14 hrs. The reaction mixture was cooled, poured on water (20 ml) and the separated residue was extracted with CHCl$_3$ (2×25 ml). The extracts were dried over Na$_2$SO$_4$ and concentrated under reduced pressure to give 1-[4-(3-chlorophenyl)piperazin-1-yl]-3-[2-oxopyrrolidin-1-yl] propane as an oil which was purified by flash column chromatography over silica gel using chloroform as eluent, yield 1.50 g (75%). IR (Neat): 3020, 2820, 1660, 1590, 1450, 1210, 730. $^1$H NMR (CDCl$_3$): 1.30–2.60(m, 12H, 3', 4', 2, 1 & 2×N-CH$_2$), 2.40–3.50(m, 8H, 5', 3 & 2×N-CH$_2$), 6.40–7.20(m, 4H, ArH). MS: m/z 321 (M+) 323 (M+2).

Mol. Formula C$_{17}$H$_{24}$ClN$_3$0: Found: C, 63.58; H, 7.82; N,13.17 Calcd.: C, 63.44; H, 7.52; N,13.06%.

(b) A mixture of 2-pyrrolidone (1 g, 12 mmol) and finely pulverized sodium metal (0.28 g, 12.0 mmcl) in dry toluene (60 ml) was heated at 120° C. with vigrous stirring for 6 hours, 1-[4-(3-chlorophenyl)piperazin-1-yl]-3-chloropropane (3.26 g, 12.0 mmol) was added to this reaction mixture and the reaction mixture was heated under stirring at 120° C. for 7 hour. The reaction mixture was filtered and toluene was removed under reduced pressure. The residue was chromatographed over flash silica gel using chloroform as eluent to give the title product, yield 2.65 g (70%), oil.

(c) A mixture of 1-chloro-3-[2-oxopyrrolidin-1-yl] propane (1.0 g, 6.2 mmol), 1-(3-chlorophenyl)piperazine (1.22 g, 6.2 minol), anhydrous Na$_2$CO$_3$ (0.33 g, 3.1 mmcl) and NaI (0.09–3 g, 0.6 mrnol) in dry toluene (10 ml) was stirred at 110° C. for 12 hrs. The solvent was removed at reduced pressure and residue was poured on water (20 ml). The separated residue was extracted with ethylacetate (3×20 ml), dried over Na$_2$SO$_4$ and concentrated under reduced pressure to give 1-[4-(3-chlorophenyl)piperazin-1-yl]-3-[2-oxopyrrolidin-1-yl]propane as an oil which was purified by flash column chromatography over silica gel using chloroform as eluent, yield 0.60 g (30.0%)

(d) A mixture of 1-chloro-3-[2-oxopyrrolidin-1-yl] propane (1 g, 6.2 mmcl), 1-(3-chlorophenyl)piperazine (1.22 g, 6.2 inmol) anhydrous Na$_2$CO$_3$ (0.33 g, 3.1 mmol) and NaI (0.093 g, 0.6 mmcl) in dry xylene (15 ml) was stirred at 150° C. for 14 hirs. The solvent was removed at reduced pressure and residue was poured on water (30 ml). The separated residue was extracted with dichloromethane (2×25 ml), dried over Na$_2$SO$_4$ and concentrated to give 1-[4-(3-chlorophenyl)piperazin-1-yl]-3-[2-oxopyrrolidin-1-yl] propane as an oil which was purified by flash column chromatography over silica gel using chloroform as fluent, yield 0.72 g (36%).

EXAMPLE 3

(a) Preparation of 1-[4-(4-chlorophenyl)piperazin-1-yl]-3-[2-oxopyrrolidin-1-yl]propane of the formula 1, where Ar=C$_6$H$_4$-4-Cl, n=1

A mixture of 1-chloro-3-[2-oxopyrrolidin-1-yl]propane (1 g, 6.2 mmol), 1-(4-chlorophenyl)piperazine (1.22 g, 6.2 mmol) anhydrous Na$_2$CO$_3$ (0.33 g, 3.1 mmol) and NaI (0.09 g, 0.6 mmol) in dry DMF (5 ml) was stirred at 70° C. for 12 hrs. The reaction mixture was cooled, poured on water (20 ml) and the separated residue was extracted with CHCl$_3$ (2×25 ml). The extracts were dried over Na$_2$SO$_4$ and concentrated under reduced pressure to give 1-[4-(4-chlorophenyl)piperazin-1-ylII-3-[2-oxopyrrolidiu-1-yl] propane which was purified by flash column chromatocjraphy over silica gel using chloroform as eluent, yield 1.48 g (74%), M.P. 78–80° C. IR (KBr): 3440, 2820, 1660, 1490, 1230, 1130, 810. $^1$H NMR (CDCl$_3$): 1.50–2.80 (m, 12H, 3', 4', 2, 1 & 2×N-CH$_2$), 3.00–3.60(m, 8H, 5', 3 & 2×N-CH$_2$), 6.80(d, 2H, J=9.0 Hz, ArH, o to Cl), 7.20(d, 2H, J=9.0 Hz, ArH, m to Cl). MS: m/z 321 (M+) 323(M±2).

Mol. formula C$_{17}$H$_{24}$ClN$_3$0: Found: C, 63.84; H, 7.32; N,13.12 Calcd.: C, 63.44; H, 7.52; N,13.06%.

(b) A mixture of 2-pyrrolidone (1 g, 12 mmol) and timely pulverized sodium metal (0.28 g, 12.0 mmol) in dry xylene (60 ml) was heated at 140° C. with vigrous stirring, 1-[4-(4-chlorophenyl)piperazin-1-yl]-3-chloropropane (3.26 g, 12.0 mmol) was added to the stirred reaction mixture after 30 minutes and the heating at 140° C. was continued for 1 hour. The reaction mixture was filtered and xylene was removed under reduced pressure to give 3 which was purified by flash column chromatography over silica gel using chloroform as eluent, yield 2.83 g (75%), M.P. 78–80° C.

(c) A mixture of 2-pyrrolidone (1 g, 12 mmol) and finely pulverized potassium metal (0.47 g, 12.0 mmol) in dry xylene (60 ml) was heated at 150° C. with vigrous stirring, 1-[4-(4-chlorophenyl)piperazin-1-yl]-3-chloropropane (3.26 g, 12.0 mmol) was added to the stirred reaction mixture after 20 minutes and the heating at 150° C. was continued for 1 hour. The reaction mixture was filtered and xylene was removed under reduced pressure to give 3 which was purified by flash column chromatography over silica gel using chloroform as eluent, yield 2.78 g (73.5%), M.P. 78–80° C.

(d) A mixture of 2-pyrrolidone (1 g, 12 mmcl) and timely pulverized potassium tert. butoxide (1.34 g, 12.0 mmol) in dry xylene (60 ml) was heated at 150° C. with vigrous stirrinq, 1-[4-(4-chlorophenyl)piperazin-1-yl]-3-chloropropane (3.26 g, 12.0 mmol) was added to the stirred reaction mixture after 2 hours and the heating at 150° C. was continued for 4 hour. The reaction mixture was filtered and xylene was removed under reduced pressure to give 3 which was purified by flash column chromatography over silica gel using chloroform as eluent, yield 2.46 g (65%), M.P. 78–80° C.

EXAMPLE 4

(a) Preparation of 1-[4-(3-fluorophenyl)piperazin-1-yl)-3-[2-oxopyrrolidin-1-yl]propane of the formula 1, where Ar=C$_6$H$_4$-3-F, n=1

A mixture of 1-chloro-3-[2-oxopyrrolidin-1-yl]propaur (1 g, 6.2 mmol), 1-(3-fluorophenyl)piperazine (1.12 g, 6.2 mmol), anhydrous K$_2$CO$_3$ (0.434 g, 3.1 mmol) and KI (0.10 g, 0.6 mmol) in dry DMF (5 ml) was stirred at 90° C. for 12 hrs. The reaction mixture was cooled, poured on water (25 ml) and the separated residue was extracted with CHCl$_3$ (2×25 ml). The extracts were dried over Na$_2$SO$_4$ and concentrated under reduced pressure to give 1-[4-(3-fluorophenyl)piperazin-1-yl]-3-[2-oxopyrrolidin-1-yl] propane as an oil which was purified by flash column chromatography over silica gel using chloroform as eluent, yield 1.32 g (69.6%). IR(Neat): 2920, 2800, 1650, 1440, 1240, 1150, 740. $^1$H NMR (CDCl$_3$): 1.50–2.70(m, 12H, 3', 4', 2, 1 & 2×N-CH$_2$), 3.00–3.60(m, 8H, 5', 3 & 2×N-CH$_2$), 6.30–6.80(m, 4H, ArH). MS: m/z 305 (M$^+$) 307 (M+2). Mol. formula C$_{17}$H$_{24}$FN$_3$0 : Found: C, 67.22; H, 7.72; N, 13.97 Calcd.: C, 66.88; H, 7.92; N, 13.76%.

(b) A mixture of 2-pyrrolidone (1 g, 12 mmol) and tinely pulverized sodium metal (0.28 g, 12.0 mmol) in dry xylene (60 ml) was heated at 150° C. with vigorous stirring, 1-[4-(3-fluorophenyl)piperazin-1-yl]-3-chloropropane (3.07 g, 12.0 mmol) was added to the stirred reaction mixture and the heating at 150° C. was continued for 1 hour. The product was obtained by the similar method as in example 3, yield 2.94 g(82%), oil.

EXAMPLE 5

(a) Preparation of 1-[4-(4-fluorophenyl)piperazin-1-yl]-3-[2-oxopyrrolidin-1-yl]propane of the formula 1, where Ar=C$_6$H$_4$-4-F, n=1

A mixture of 1-chloro-3-[2-oxopyrrolidin-1-yl]propaxie (4 g, 25.0 mmol), 1-(4-fluorophenyl)piperazine (4.47 g, 25.0 mmol), anhydrous Na$_2$CO$_3$ (1.325 g, 12.5 mmol) and NaI (0.38 g, 2.5 mmol) in dry DMF (20 ml) was stirred at 120° C. for 8 hrs. The reaction mixture was cooled, poured on water (30 ml) and the separated residue was extracted with CHCl$_3$ (2×30 ml). The extracts were dried over Na$_2$SO$_4$ and concentrated under reduced pressure to give 1-[4-(4-fluorophenyl)piperazin-1-yl]-3-[2-oxopyrrolidin-1-yl]-propane as an oil which was purified by flash column chromatography over silica gel using chloroform as eluent, yield 5.72 g (75.5%). IR (Neat): 2920, 2820, 1660, 1500, 1250, 730. $^1$H NMR (CDCl$_3$): 1.50–2.80(m, 12H, 3', 4', 2, 1 & 2×N-CH$_2$), 3.00–3.60(m, 8H, 5', 3 & 2×N-CH$_2$), 6.70–7.10(m, 4H, ArH). MS: m/z 305 (M$^+$). Mol. formula C$_{17}$H$_{24}$FN$_3$0 : Found: C, 66.55; H, 8.07; N, 13.69 Calcd.: C, 66.86; H, 7.92; N, 13.76%.

(b) A mixture of 2-pyrrolidone (3 g, 35 mmol) and finely pulverized sodium metal (0.81 g, 35.0 mmol) in dry xylene (180 ml) was heated at 150° C. with vigorous stirring, 1-[4-(4-fluorophenyH,piperazin-1-yl]-3-chloropropane (8.96 g, 35.0 mmol) was added to the stirred reaction mixture after 30 minutes and the heating at 150° C. was continued for 1 hour. The reaction mixture was filtered and xylene was removed under reduced pressure to give 3 which was purified by flash column chromatography over silica gel using chloroform as eluent, yield 9.15 g (85%), oil.

EXAMPLE 6

(a) Preparation of 1-[4-(4-ethylphenyl)piperazin-1-yl]-3-[2-oxopyrrolidin-1-yl]propane of the formula 1, where Ar=C$_6$H$_4$-4-C$_2$H$_5$, n=1

A mixture of 1-chloro-3-[2-oxopyrrolidin-1-yl]propane (2.0 g, 12.0 mmol), 1-(4-ethylphenyl)piperazine (2.36 g, 12.0 mmol), anhydrous Na$_2$CO$_3$ (0.658 g, 6.2 mmol) and NaI (0.18 g, 1.2 mmol) in dry DMF (10 ml) was stirred at 80° C. for 12 hrs. The reaction mixture was cooled, poured on water (30 ml) and the separated residue was extracted with CHCl$_3$ (2×30 ml). The extracts were dried over Na$_2$So$_4$ and concentrated under reduced pressure to give 1-[4-(4-ethylphenyl)piperazin-1-yl]-3-[2-oxopyrrolidin-1-yl] propane as an oil which was purified by flash column chromatography over silica gel using chloroform as eluent, yield 2.43 g (62.0%). IR (Neat): 2940, 2800, 1660, 1440, 1000, 900,800. $^1$H NMR (CDCl$_3$): 1.20(t, 3H, J=6.0 Hz, CH$_2$CH$_3$, 1.60–280(m, 14H, 3',4',2,1 & 2×N—CH$_2$, CH$_2$CH$_3$), 3.00–3.60(m, 8H, 5', 3 & 2×N—CH$_2$). MS: m/z 315 (M$^+$).

Mol. formula C$_{19}$H$_{29}$N$_3$0: Found : C, 71.91; II, 9. 16; N, 13. 15 Calcd.: C, 72.34; H, 9.27; N, 13.32%.

(b) A mixture of 2-pyrrolidone (2 g, 24 mmol) and finely pulverized sodium metal (0.56 g, 24.0 mmcl) in dry xylene (120 ml) was heated at 150° C. with vigrous stirring, 1-[4-(4-ethylphenyl)piperazin-1yl]-3-chloropropane (6.38 g, 24.0 mmol) was added to the stirred reaction mixture after 30 minutes and the heating at 150° C. was continued for 1 hour. The product was obtained by the similar method as in example-3, yield 6.42 g (78%), oil.

EXAMPLE 7

(a) Preparation of 1-[4-(2-ethylphenyl)piperazin-1-Yl]-3-[2-oxopyrrolidin-1-yl]propane of the formula 1, where Ar=C$_6$H$_4$-2-C$_2$H$_5$, n=1

A mixture of 1-chloro-3-[2-oxopyrrolidin-1-yl]propane (2.0 g, 12.0 mmol), 1-(2-ethylphenyl)piperazine (2.36 g, 12.0 mmol), anhydrous Na$_2$CO$_3$ (0.658 g, 6.2 mmol) and NaI (0.18 g, 1.2 mmol) in dry DMF (10 ml) was stirred at 80° C. for 12 hrs. The reaction mixture was cooled, poured on water (30 ml) and the separated residue was extracted with CHCl$_3$ (2×20 ml). The extracts were dried over Na$_2$So$_4$and concentrated under reduced pressure to give 1-[4-(4-ethylphenyl)piperazin-1-yl]-3-[2-oxopyrrolidin-1-yl]propane as an oil which was purified by flash column chromatography over silica gel using chloroform as eluent, yield 2.17 g (60.0%). IR (Neat): 2940, 2820, 1660, 1430, 1010, 900, 800. $^1$H NMR (CDCl$_3$): 1.24(t, 3H, J=6 Hz, CH$_2$—CH$_3$), 1.68–1.85(m, 2H, 4'-CH$_2$), 1.98–2.10(m, 2H, 2-CH$_2$), 2.34–2.50(m, 4H, 3' & 1-CH$_2$), 2.62(bs, 4H, 2×N—CH$_2$), 2.68(q, 2H, CH$_3$—CH$_2$), 2.94(t, 4H, J=G.0 Hz, 2×N—CH$_2$), 2.35(t, 2H, ,J=6.0 Hz, 3-CH$_2$), 3.42 (t, 2H, J=6.0 Hz. 5'-CH$_2$), 7.00–7.28(m, 4H, Ar—H). MS: m/z 315 (M$^+$).

Mol. formula C$_{19}$H$_{29}$N30: Found: C, 72.64; H, 9.11; N, 13.64 Calcd.: C, 72.34; H, 9.27; N, 13.32%

(b) A mixture of 2-pyrrolidone (1 g, 12 mmol) and tinely pulverized sodium metal (0.28 g, 12.0 mmol) in dry xylene (60 ml) was heated at 150° C. with vigorous stirring, ethylphenyl)piperazin-1-yl]-3-chloropropane (3.19 g, 12.0 mmcl) was added to the stirred reaction mixture after 30 minutes and the heating at 150° C. was continued for 1 hour. The product was obtained by the similar method as in example-3, yield 3.13 g (76%), oil.

EXAMPLE 8

(a) Preparation of 1-[4-(4-chlorophenyl)piperazin-1-yl]-3-[2-oxopiperidin-1-yl]propane of the formula 1, where Ar=C$_6$H$_4$-4-Cl, n=2

A mixture of 2-piperidone (1 g, 10 mmol) and finely pulverized sodium metal (0.23 g, 10 mmol) in dry xylene (60 ml) was heated at 140° C. with vigorous stirring, 1-[4-(4-chlorophenyl)piperazin-1-yl]-3-chloropropane (2.72 g, 10 mmol) was added to the stirred reaction mixture after 30 minutes and the heating at 140° C. was continued for 1 hour. The reaction mixture was filtered and xylene was removed under reduced pressure to give 3 which was purified by flash column chromatography over silica gel using chloroform as eluant, yield 2.54 g (75%), m.p. 106° C. IR (Neat): 3761, 3408, 3017, 2957, 2882, 2826, 2785, 2502, 1659, 1599, 1499, 1456, 1385, 1346, 1219, 1148, 1105, 760, 667. PMR (CDCl$_3$): 0.89–1.80(m, 6H, 4',5' & 2-CH$_2$), 2.33–2.65(m, 8H, 3',1 & 2×N—CH$_2$), 3.1573.62(m, 8H, 6',3 & 2×N (CH$_2$), 6.81 7.00(2×dd, 4×ArH). MS: m/z 337 (M+2). Mol. formula C$_{18}$H$_{26}$N$_3$0C1 : Found: C, 64.23; H, 7.87; N, 12.24 Calcd.: C, 64.37; H, 7.80; N,12.51%.

(b) A mixture of 2-piperidone (1.0 g, 10 mmol) and tiliely pulverized potassium tert. butoxide (1.12 g, 10 mmol) in dry xylene (60 ml) was heated at 150° C. with vigrous stirring, 1-[4-(4-chlorophenyl)piperazin-1-yl]-3-chloropropane (2.72 g, 10 mmol) was added to the stirred reaction mixture after 2 hours and the heating at 150° C. was continued for 4-hour. The reaction mixture was filtered and xylene was removed under reduced pressure to give 3 which was purified by flash column chromatography over silica gel using chloroform as eluant, yield 2.17 g (64%) m.p. 106° C.

EXAMPLE 9

Preparation of 1-[4-(3-chlorophenyl)piperazin-1-yl]-3-[2-oxopiperidin-1-yl]propane of the formula 1, where Ar=$C_6H_4$-3-Cl, n=2

A mixture of 2-piperidone (1.0 g, 10 mmol) and finely pulverized sodium metal (0.23 g, 10 mmol) in dry toluene (60 ml) was heated at 120° C. with vigrous stirring for 6 hours, 1[4-(3-chlorophenyl)piperazin-1-yl]-3-chloropropane (2.72 g, 10 mmol) was added to this reaction mixture and the reaction mixture was heated under stirring at 1200 £ for 7 hour. The reaction mixture was filtered and toluene was removed under reduced pressure. The residue was chromatographed over flash silica gel using chloroform as eluant to give 3, yield 2.59 g (76.5%), oil. IR (Neat): 3406, 2951, 2878, 1626, 1597, 1491, 1454, 1383, 1352, 1219, 1142, 1103. $^1$H NMR (CDCl$_3$): 1.17–1.84(m, 6H, 2, 4' & 5'-CH$_2$), 2.27–2.65(m, 8H, 1, 3' & 2×N—CH$_2$), 3.15–3.37 (m, 8H, 6', 3 & 2×N—CH$_2$), 6.68–6.79(dd, 2×ArH), 7.05–7.11(t, 1×ArH), 7.19(s, 1×ArH). MS: m/z 335 (M$^+$).
Mol. formula $C_{18}H_{26}N_3OCl$: Found: C, 64.17; H, 7.92; N, 12.21 Calcd.: C, 64.37; H, 7.80; N, 12.51%.

EXAMPLE 10

(a) Preparation of 1-[4-(4-fluorophenyl)piperazin-1-yl]-3-[2-oxopiperidin-1-yl]propane of the formula 1, where Ar=$C_6H_4$-4-F, n=2

A mixture of 2-piperidone (2 g, 20 mmol) and finely pulverized sodium metal (0.46 g, 20 mmcl) in dry xylene (120 ml) was heated at 150° C. with vigorous stirring, 1-[4-(4-fluorophenyl)piperazin-1-yl]-3-chloropropane (5.17 g, 20 mmol) was added to the stirred reaction mixture after 30 minutes heating at 150° C. was continued for 1 hour. The reaction mixture was filtered and xylene was removed under reduced pressure to give 3 which was purified by flash column chromatography over silica gel using chloroform as eluant, yield 4.64 g (72%), oil. IR (Neat): 3408, 3014, 2931, 2880, 2825, 1626, 1508, 1458, 1219, 824, 760, 667. $^1$H NMR (CDCl$_3$): 1.72–1.86(in, 6H, 4', 5' & 2-CH$_2$), 2.37–2.69 (m, 8H, 3', 1 & 2×N—CH$_2$), 3.12–3.46(m, 8H, 6', 3 & 2×N—CH$_2$), 6.83–7.00(2×dd, 4×ArH). MS: 319 (M$^+$).
Mol. formula $C_{19}H_{26}N_3OF$: Found: C, 71.23; H, 8.26; N, 12.95 Calcd.: C, 71.47; H, 8.15; N, 13.17%.

(b) A mixture of 1-chloro-3-[2-oxopiperidin-1-yl]propane (2.1 g, 12 mmol), 1-(4-fluorophenyl)piperazine (2.16 g, 12 mmol), anhydrous Na$_2$CO$_3$ (0.618 g, 6.2 mmol) and NaI (0.18 g, 1.2 mmol) in dry DMF (10 ml) was stirred at 800 £ for 14 hrs. The reaction mixture was cooled, poured on water (30 ml) and the separated residue was extracted with CHCl$_3$ (2×35 ml). The extracts were dried over Na$_2$SO$_4$ and concentrated under reduced pressure to give 1-[4-(4-fluorophenyl)piperazin-1-yl]-3-[2-oxopiperidin-1-yl] propane as an oil which was purified by column chromatography over silica gel using chloroform as eluent, yield 2.40 g (63.0%).

EXAMPLE 11

Preparation of 1-[4-(2-ethylphenyll)piperazin-1-yl]-3-[2-oxopiperidin-1-yl]propane of the formula 1, where Ar=$C_6H_4$-2-$C_2H_5$, n=2

A mixture of 2-piperidone ( 1.0 g, 10 mmol) and finely pulverized sodium metal (0.23 g, 10 mmol) in dry xylene (60 ml) was heated at 150° C. with vigorous stirring, ethylphenyl)piperazin-1-yl]-3-chloropropane (2.66 g, 10 mmol.) was added to the stirred reaction mixture after 30 minutes and the heating at 150° C. was continued for 1 hour. The reaction mixture was filtered and xylene was removed tinder reduced pressure to give 3 which was purified by flash column chromatography on silica gel using chloroform as eluant, yield 2.49 g (75%), oil. IR (Neat): 3680, 3440, 3000, 2960, 2870, 2820, 1620, 1490, 1450, 1350, 1210, 1140, 1005, 920, 725. $^1$H NMR (CDCl$_3$): 1.00(t, 3H, CH$_2$CH$_3$), 1.20–1.90(m, 6H, 4', 5' & 2-CH$_2$), 2.20–3.50(m, 18H, 3', 6', 3, 1 & 4×N—CH2, CH$_2$CH$_3$), 7.00–7.20(m, 4H, ArH). MS: m/z 329 (M$^+$).
Mol. formula $C_{20}H_{31}N_3$: Found: C, 72.67; H, 9.60; N, 12.49 Calcd: C, 72.95; H, 9.42; N, 12.77%.

EXAMPLE 12

Preparation of 1-[4-(2-methoxyphenyl)piperazin-1-yl]-3-[2-oxopiperidin-1-yl]propane of the formula 1, where Ar=C6H5-2-OCH$_3$, n=2

A mixture of 2-piperidone ( 1.0 g, 10 mmol) and finely pulverized potassium metal (0.40 g, 10 mmol) in dry xylene (60 ml) was heated at 150 CC with vigrous stirring, 1-[4-(2-methoxyphenyl)piperazin-1-yl]-3-chloropropane (2.52 g, 10 mmol) was added to the stirred reaction mixture after 20 minutes and the heating at 150° C. was continued for 1 hour. The reaction mixture was filtered and xylene was removed under reduced pressure to give 3 which was purified by flash column chromatography over silica gel using chloroform as eluant, yield 2.41 g (72%), oil. IR (Neat): 2945, 1626, 1500, 1460, 1242, 908, 735, 648. PMR (CDCl$_3$): 1.69–1.84(m, 611, 4', 5' & 2-CH$_2$), 2.26–2.70(m, 8H, 3', 1 & 2×N—CH$_2$), 3.07–3.36(m, 8H, 6', 3 & 2×N—CH$_2$), 3.75(s, 3H, OCH$_3$), 6.76–6.95(m, 4H, ArH). MS: m/z 331 (M$^+$).
Mol. formula $C_{19}H_{29}N_3O_2$: Found: C, 68.61; H, 8.92; N, 12.56 Calcd.: C, 68.85; H, 8.81; N, 12.68%.

EXAMPLE 13

Preparation of 1-[4-(2-pyridyl)piperazin-1-yl]-3-[2-oxopiperidin-1-yl]propane of the formula 1, where Ar=2-pyridyl, n=2

A mixture of 2-piperidone (2 g, 20 mmol) and finely pulverized sodium metal (0.46 q, 20 mmol) in dry xylene ( ml) was heated at 150° C. with vigorous stirring, 1[4-2 (pyridyl)piperazine-1-yl]-3-chloropropane (4.78 g, 20 mmol) was added to the reaction mixture after 30 minutes and the heating at 150° C. was continued for 1 hour. The reaction mixture was filtered and xylene was removed under reduced pressure to give 3 which was purified by flash column chromatography over silica gel using chloroform as eluant, yield 4.39 g (72%), oil. IR (Neat): 3420, 2940, 2800, 1629, 1580, 1470, 1420, 1230, 1150, 1125, 960, 720. $^1$H NMR (CDCl$_3$): 1.50–2.20(m, 6m, 4', 5' & 2-CH$_2$), 2.25–2.80 (m, 8H, 3', 1 & 2×N—CH$_2$), 3.10–4.80(m, 8H, 6', 3 & 2×N—CH$_2$), 6.48–6.75(m, 2H, 3,5-pyridyl H), 7.40(m, 1H, 4-pyridyl H), 8.15(m, 1H, 6-pyridyl H). MS: m/z 302 (M$^+$).
Mol. formula $C_{17}H_{26}N_4O$ : Found: C, 67.32; 11, 8.49; N, 18.38 Calcd.: C, 67.52; 11, 8.67; N, 18.53%.

EXAMPLE 14

Preparation of 1-[4-(3-trifluoromethylphenyl)piperazin-1-yl]-3-[2-oxopiperidin-1-yl]propane of the formula 1, where Ar=$C_6H_4$-3-$CF_3$, n=2

A mixture of 2-piperidone (1.0 g, 10 mmol) and finely fulverized sodium metal (0.23 g, 10 mmol) in dry xylene (60 ml) was heated at 150° C. with vigorous stirring, 1-[4-(3-CF$_3$-phenyl)piperazin-1-yl]-3-chloropropane (3.06 g, 10 mmol) was added to the stirred reaction mixture after 30 minutes and the heating at 150° C. was continued for 1 hour. The reaction mixture was filtered and xylene was furnished by flush column chromatography on silica gel using CHC13 as eluant, yield 2.80 g (75%), oil. IR (Neat): 3402, 3015, 2951, 2880, 2827, 2785, 1622, 1449, 1450, 1352, 1315, 1217, 1167, 1126, 1076, 997, 951. $^1$H NMR (CDCl$_3$): 1.75–1.93(m, 6H, 4', 5' & 2-CH$_2$), 2.35–2.75(m, PH, A,1 & 2×N—CH$_2$), 3.310–3.84(m, 8H, 6', 3 & 2×N—CH$_2$), 7.04–7.10(dd, 2H, 4, 6-ArH), 7.26(s, H, 2-ArH), 7.32–7.37 (t, H, 5-ArH). MS: m/z 369(M$^+$).

Mol. formula $C_{16}H_{26}N_3OF_3$: Found: C, 61.48; H, 7.23; N, 11.21 Calcd.: C, 61.79; H, 7.05; 11.38%.

EXAMPLE 15
Antihypertensive/hypotensive activity (a) Cats (2.6–4.0 kg) of either sex anaesthetized with pentobarbitone sodium (40 mg/kg i.v.) and showing basal mean arterial blood plessure below 150 mm (Hg) were categorised as normotensive and ahove 150 mm Hg as hypertensive. Arterial blood pressure (EP) was recorded from one of the carotid artery through a stathum P23 DC pressure transducer and 7P1 low level DC preamplifier on a Grass Model P7 Polygraph, Signals from 7P1 preamplifier were used to trigger 7P4 Tachograph preamplifier for recording the heart rate (HR). Right femoral vein and Trachea were cannulated for intravenous injections and artificial ventilation respectively. Control responses to intravenous injection of noradrenaline (2–4 ug); acetyl choline (1–2 ug); histamine (1–2 ug) and isoprenaline (1–2 ug) were taken before and after the administration of test doses of each compounds. All the compounds were tested at fixed doses of 2.0 and 10 uM/kg i.v. Significant results are given in Table 2.

What is claimed is:

1. A propane compound of 1-[4-arylpiperazin-1-yl]-3-[2-oxopyrrolidin-1-yl ]propane or 1-[4-arylpiperazin-1-yl]-3-[2-oxopiperidin-1-yl ]propane having formula I:

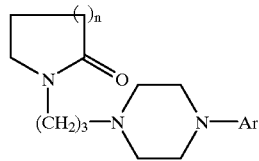

wherein Ar represents pyridyl, or a phenyl ring substituted with trifluoromethyl halogen, alkoxy, or alkyl, and n is 1 or 2.

2. The compound of claim 1, wherein the halogen is selected from the group consisting of chlorine, fluorine, bromine, and iodine, and mixtures thereof, the alkoxy is $C_1$–$C_{10}$oxy, the alkyl is $C_1$–$C_{10}$alkyl, and the heteroaryl is a pyridyl ring.

3. The compound of claim 1 wherein the propane compound is selected from the group consisting of:

(a) 1-[4-(3-chlorophenyl)piperazin-1-yl]-3-[2-oxopyrrolidin-1-yl]propane;
(b) 1-[4-(4-chlorophenyl)piperazin-1-yl]-3-[2-oxopyrrolidin-1-yl]propane;
(c) 1-[4-(3-fluorophenyl)piperazin-1-yl]-3-[2-oxopyrrolidin-1-yl]propane;
(d) 1-[4-(4-fluorophenyl)piperazin-1-yl]-3-[2-oxopyrrolidin-1-yl]propane;
(e) 1-[4-(4-ethylphenyl)piperazin-1-yl]-3-[2-oxopyrrolidin-1-yl]propane;
(f) 1-[4-(2-ethylphenyl)piperazin-1-yl]-3-[2-oxopyrrolidin-1-yl]propane;
(g) 1-[4-(4-chlorophenyl)piperazin-1-yl]-3-[2-oxopiperidin-1-yl]propane;
(h) 1-[4-(3-chlorophenyl)piperazin-1-yl]-3-[2-oxopiperidin-1-yl]propane;
(i) 1-[4-(4-fluorophenyl)piperazin-1-yl]-3-[2-oxopiperidin-1-yl]propane;
(j) 1-[4-(2-ethylphenyl)piperazin-1-yl]-3-[2-oxopiperidin-1-yl]propane;
(k) 1-[4-(2-methoxyphenyl)piperazin-1-yl]-3-[2-oxopiperidin-1-yl]propane;
(l) 1-[4-(2-pyridyl)piperazin-1-yl]-3-[2-oxopiperidin-1-yl]propane; and
(m) 1-[4-(3-trifluoromethylphenyl)piperazin-1-yl]-3-[2-oxopiperidin-1-yl]propane.

4. A pharmaceutical composition comprising a compound of formula I:

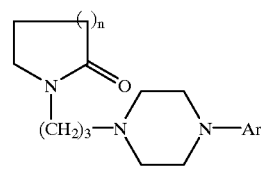

wherein Ar represents a phenyl ring substituted with trifluoromethyl, halogen, alkoxy, or alkyl groups, or Ar represents a pyridyl ring, and n is 1 or n is 2.

5. The pharmaceutical composition of claim 4 wherein the halogen is selected from the group consisting of chlorine, fluorine, bromine, and iodine, and mixtures thereof, the alkoxy is $C_1$–$C_{10}$oxy, the alkyl is $C_1$–$C_{10}$alkyl, and the heteroaryl is a pyridyl ring.

6. The composition of claim 4 wherein the propane compound is selected from the group consisting of:

(a) 1-[4-(3-chlorophenyl)piperazin-1-yl]-3-[2-oxopyrrolidin-1-yl]propane;
(b) 1-[4-(4-chlorophenyl)piperazin-1-yl]-3-[2-oxopyrrolidin-1-yl]propane;
(c) 1-[4-(3-fluorophenyl)piperazin-1-yl]-3-[2-oxopyrrolidin-1-yl]propane;
(d) 1-[4-(4-fluorophenyl)piperazin-1-yl]-3-[2-oxopyrrolidin-1-yl]propane;
(e) 1-[4-(4-ethylphenyl)piperazin-1-yl]-3-[2-oxopyrrolidin-1-yl]propane;
(f) 1-[4-(2-ethylphenyl)piperazin-1-yl]-3-[2-oxopyrrolidin-1-yl]propane;
(g) 1-[4-(4-chlorophenyl)piperazin-1-yl]-3-[2-oxopiperidin-1-yl]propane;
(h) 1-[4-(3-chlorophenyl)piperazin-1-yl]-3-[2-oxopiperidin-1-yl]propane;
(i) 1-[4-(4-fluorophenyl)piperazin-1-yl]-3-[2-oxopiperidin-1-yl]propane;
(j) 1-[4-(2-ethylphenyl)piperazin-1-yl]-3-[2-oxopiperidin-1-yl]propane;
(k) 1-[4-(2-methoxyphenyl)piperazin-1-yl]-3-[2-oxopiperidin-1-yl]propane;
(l) 1-[4-(2-pyridyl)piperazin-1-yl]-3-[2-oxopiperidin-1-yl]propane; and
(m) 1-[4-(3-trifluoromethylphenyl)piperazin-1-yl]-3-[2-oxopiperidin-1-yl]propane.

7. A method of treating hypertension in mammals that comprises administering to a patient in need thereof a therapeutically effective amount of a compound according to claim 1.

8. A method of treating peripheral vascular diseases in mammals that comprises administering to a patient in need thereof a therapeutically effective amount of a compound according to claim 1.

9. A method of treating a condition arising out of alterations in a central circulation, peripheral circulation, or adrenergic receptor system that comprises administering to a subject suffering from said condition a therapeutically effective amount of a compound according to claim 1, wherein said condition comprises myocardial ischemia, myocardial infarction, angina pectoris, any cardiac surgical interventions, renal ischemia, circulatory insufficiency in extremities, stroke or trauma.

10. A method of treating reperfusion injury in mammals that comprises administering to a patient in need thereof a therapeutically effective amount of a compound according to claim 1.

11. A method of treating ischemic diseases in mammals that comprises administering to a patient in need thereof an effective amount of a compound according to claim 1.

12. The method of claim 11, wherein the ischemic diseases are selected from the group comprising myocardial infarction (MI), angina pectoris, or cardiac surgical intervention.

* * * * *